(12) United States Patent
Yao et al.

(10) Patent No.: US 9,526,722 B1
(45) Date of Patent: Dec. 27, 2016

(54) ONCOGENIC ROS1 KINASE INHIBITOR

(71) Applicant: Macau University of Science and Technology, Macau (MO)

(72) Inventors: Xiao Jun Yao, MO (MO); Lai Han Leung, MO (MO); Lian Xiang Luo, MO (MO); Yan Ling Zhou, MO (MO); Liang Liu, MO (MO)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 14/744,042

(22) Filed: Jun. 19, 2015

(51) Int. Cl.
*A01N 43/42* (2006.01)
*A61K 31/444* (2006.01)
*A61K 31/4745* (2006.01)

(52) U.S. Cl.
CPC .................. *A61K 31/4745* (2013.01)

(58) Field of Classification Search
CPC . A61K 31/4745; C07D 495/14; C07D 513/04; C12N 2310/321; C12N 2310/346; C12N 2310/341

See application file for complete search history.

(56) References Cited

PUBLICATIONS

Mazieres et al. JCO, Feb. 2015.*
Lim et al, PLOS ONE, Sep. 14, 2015.*
Freshney (Culture of Animal Cells, A Manual of Basic Technique, Alan R. Liss, Inc., 1983, New York, p. 4).*
Dermer (Bio/Technology, 1994, 12:320).*
Gura (Science, v278, 1997, pp. 1041-1042).*

* cited by examiner

*Primary Examiner* — Jean Cornet
(74) *Attorney, Agent, or Firm* — Renner Kenner Greive Bobak Taylor & Weber (57) ABSTRACT

The present invention provides a compound that inhibits activity of oncogenic ROS1, a composition comprising said compound. The present invention also provides the use of said composition for treating cancer.

3 Claims, 7 Drawing Sheets

ONCOGENIC ROS1 KINASE INHIBITOR

FIELD OF INVENTION

The present invention relates to compound that inhibits ROS1 kinase activity, composition comprising said compound and the use of said compound for treating cancer.

BACKGROUND OF INVENTION

Receptor tyrosine kinases (RTKs) are vital mediators of extracellular signals, which direct cell growth, survival and motility pathways. Several pathogenesis including chromosomal rearrangements, gene amplification, and point mutations result in abnormal and constitutive RTK activation which is in turn responsible for initiation and progression of many cancers, including non-small cell lung cancer (NSCLC). The first targetable fusion gene of RTK identified in NSCLC is Echinoderm microtubule associated protein like 4 ((EML4)-ALK). Oncogenic c-ros oncogene1 (ROS1) RTK is later reported to be fused with other forms of lung constitutive expressed 5' or 3'-fusion gene partners in NSCLC. Approximately 1~2% of NSCLC patients harbor multiple kinds of ROS1 chromosome rearrangement. Recent developments in targeted-based therapies have led to a major paradigm shift in oncology. Small-molecule tyrosine kinase inhibitors are applied to treat cancer patients who have tyrosine kinase gene fusions. Several tyrosine kinase inhibitors have been shown to have promising effect in the clinical practice. For example, Crizotinib, a potent ATP-competitive small molecule inhibitor of ALK, have now been approved by the FDA for treating NSCLC patients that are ALK rearrangement-positive. Crizotinib displays marked anti-tumor activity both in vitro and in vivo as well as in clinical practices. Since the tyrosine kinase domains of ALK and ROS1 are very similar, with 77% identity within the ATP-binding sites, most ALK inhibitors have cross activity against ROS1. In one early clinical trial of crizotinib to treat NSCLC patients harboring ROS1 rearrangements, the objective response rate was 72%, the median duration of response was 17.6 months and median progression-free survival was 19.2 months. Although most patients with ROS1-positive NSCLC exhibit substantial clinical benefit from Crizotinib, the efficacy of Crizotinib is limited by the development of acquired drug resistance. Accordingly, there is a need for new compound targeting ROS1 for cancer treatment.

SUMMARY OF INVENTION

The first aspect of the present invention relates to a compound having structure of Formula I, The second aspect of the present invention relates to a composition comprising the compound of Formula I. One embodiment of the second aspect of the present invention relates to use of the composition comprises the compound of Formula I to inhibit activity of oncogene receptor tyrosine kinase (ROS1). The composition inhibits ROS1 kinase activity and suppresses phosphorylation of ROS1, as well as anti-apoptotic and growth signaling downstream to ROS1.

The third aspect of the present invention relates to a method of treating cancer comprising administering a composition comprises a compound of Formula I to a subject in need thereof. The subject in need thereof is a subject having an abnormality in ROS1 gene. The abnormality of ROS1 gene may be ROS1 chromosome rearrangement and/or ROS1 gene fusion. The subject in need thereof is ROS1-positive NSCLC individual. In one embodiment of the third aspect of the present invention, the cancer treated is non-small cell lung cancer (NSCLC).

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Unless otherwise defined, all technical terms used herein have the same meaning as commonly understood to one of ordinary skill in the art to which the invention belongs.

Other and advantages of the invention will be apparent to those skilled in the art from a review of the ensuing description.

BRIEF DESCRIPTION OF DRAWINGS

FIG. 1 shows the cell viability of HCC78 cells (FIG. 1A) and BEAS-2B cells (FIG. 1B) after 72 hours treatment with compound of Formula I of the present invention.

FIG. 2 shows florescence images (FIG. 2A) and cytogram pattern (FIG. 2B) of HCC78 cells having treated with compound of Formula I of the present invention.

FIG. 5 shows 3D schematic representation of the compound of Formula I binds to ROS1 (FIG. 5A) and (FIG. 5B).

DETAILED DESCRIPTION OF INVENTION

The present invention is not to be limited in scope by any of the specific embodiments described herein. The following embodiments are presented for exemplification only.

The present invention provides a compound of Formula I,

The present compound of Formula I is a potent inhibitor of ROS1 oncogene receptor tyrosine kinase (ROS1). The present compound binds to ROS1 and inhibits kinase activity of ROS1 and suppresses ROS1 phosphorylation. Anti-apoptotic and growth signalings downstream of ROS1 are also inhibited by the compound of Formula I of the present invention.

The second aspect of the present invention relates to a composition comprising the compound of Formula I. One embodiment of the second aspect of the present invention relates to use of the composition comprises the compound of Formula I to inhibit activity of ROS1 oncogene receptor tyrosine kinase (ROS1). The composition inhibits ROS1 kinase activity and suppresses phosphorylation of ROS1, as well as anti-apoptotic and growth signaling downstream to ROS1.

The third aspect of the present invention relates to a method of treating cancer comprising administering a composition comprises a compound of Formula I to a subject in need thereof. The subject in need thereof is a subject having an abnormality in ROS1 gene. The abnormality of ROS1 gene is oncogenic result by ROS1 chromosome rearrangement and/or ROS1 gene fusion. The subject in need thereof is a ROS1-positive NSCLC individual. In one embodiment of the third aspect of the present invention, the cancer treated is non-small cell lung cancer (NSCLC). The ROS1 gene rearrangements in NSCLC have been widely studied in large scale screening study through RT-PCR and DNA sequencing in NSCLC cell lines and NSCLC patients. The ROS1 gene rearrangements are readily known in the art. One common example of ROS1 gene rearrangements involve fusion of SLC34A2-ROS1 and CD74-ROS1. The CD74 gene encodes a type 2 transmembrane protein that fuses with ROS1 to generate a CD74-ROS1 transcript found to be the most common form of all ROS1 fusion genes in NSCLC, accounting for about 40% of all ROS1 fusions genes in NSCLC.

Figure 1A:
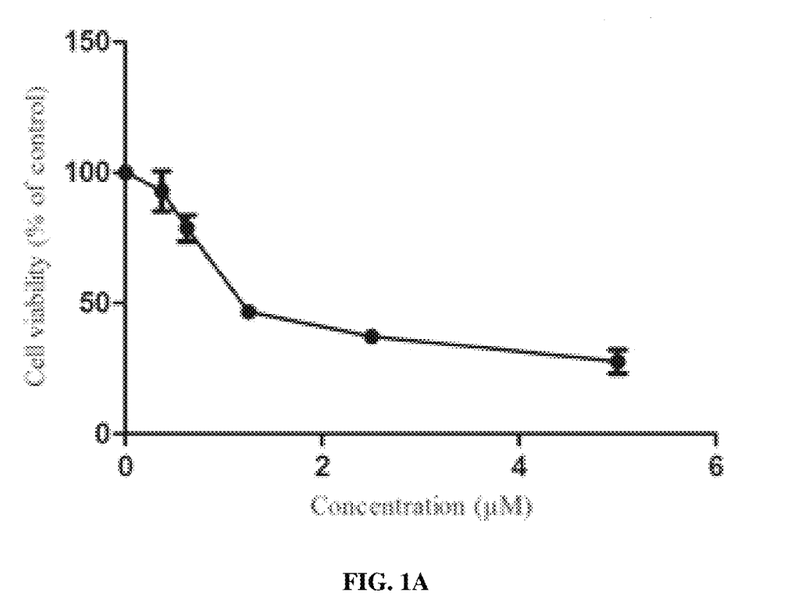
Figure 1B:
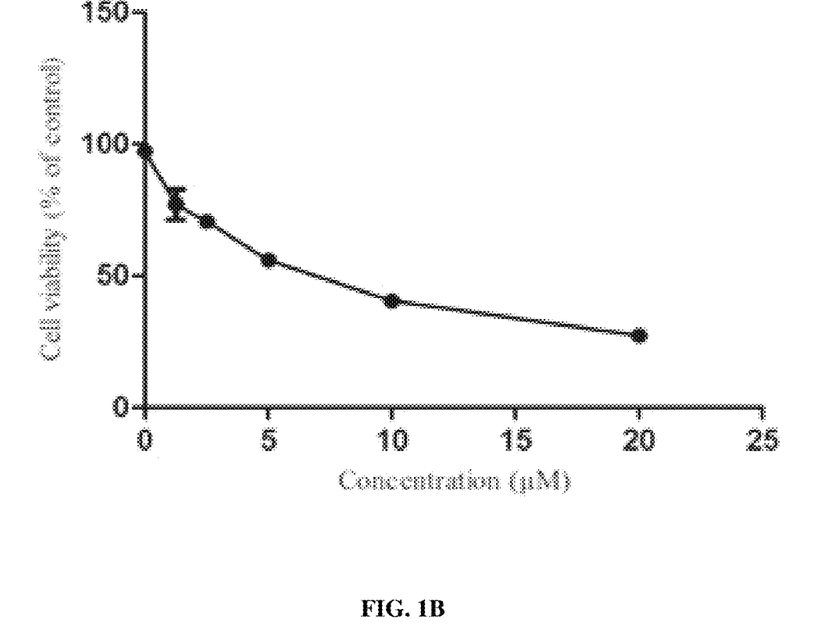

The compound of formula I of the present invention is shown to be highly cytotoxic and selective to cancer cells. The present compound of Formula I has little effect on healthy normal non-cancerous cells. To show the highly cytotoxic and selective properties of the present compound of Formula I, HCC78 NSCLC cells and normal lung epithelial cells (BEAS-2B) are treated with the compound of the present invention and effects are observed. HCC78 NSCLC cells are non-small cell lung cancer cells with a ROS1 gene fusion. HCC78 cells are obtained from the ATCC and cultured in environment of 5% CO2 at 37° C. in RPMI-1640 medium supplemented with 10% fetal bovine serum (FBS), 100 units/mL penicillin, and 100 μg/mL streptomycin, The compound of Formula I is dissolved in DMSO. Using a MTT assay, 3000 HCC78 or BEAS-2B cells are seeded on 96-well plates, cultured overnight for cell adhesion, and treated with DMSO or various concentrations of the present compound of Formula I for 72 h. Triplicate are performed. 10 μL of MTT (5 mg/mL; Sigma) are added to each well, and incubation continues for another 4 hours. Then the dark blue crystals are dissolved in 100 μL of the resolved solution (10% SDS and 0.1 mM HCL). The absorbance is measured at 570 nm by a microplate reader (Tecan, Morrisville, N.C., USA). The cell viability is calculated relative to untreated controls, with results based on at least 3 independent experiments. The MTT assay shows that compound of Formula I is a potent inhibitor of HCC78 cells with a $IC_{50}$ of G341-0312 is 1.62 μM±0.39 μM, while it shows much lower cytotoxicity on normal lung epithelial cells (BEAS-2B) after 72 hr treatment, with a $IC_{50}$ in BEAS-2B is 6.08 μM±1.16 μM (FIG. 1A and FIG. 1B). The present compound of Formula I exerts a 3.75 fold cytotoxicity towards cancer cells than normal healthy cells. The present compound of Formula I is highly selectively towards cancer cells.

Figure 2A:
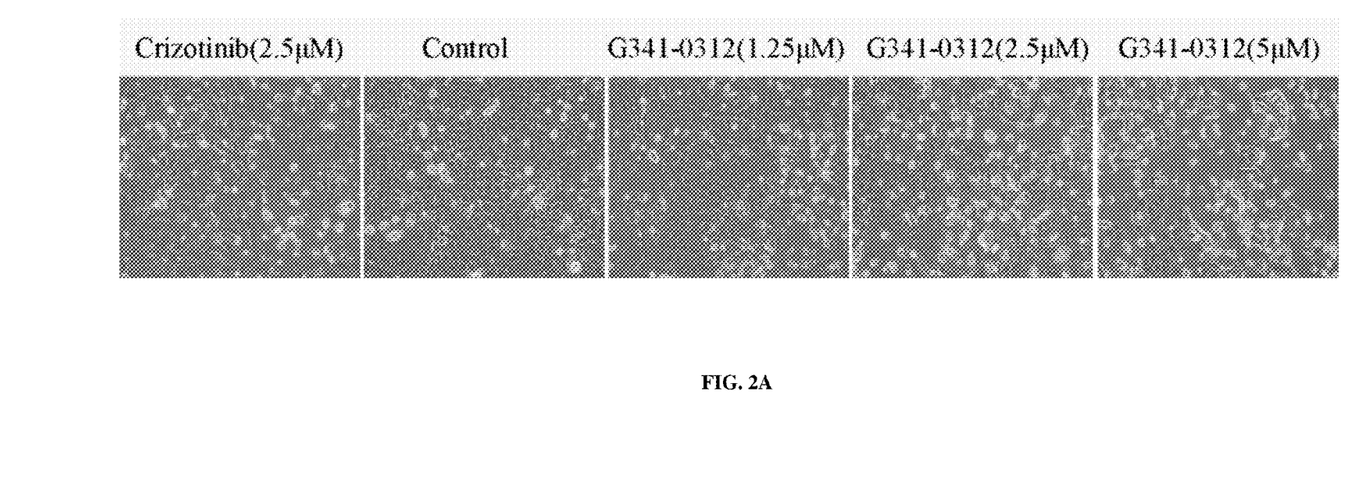
Figure 2B:
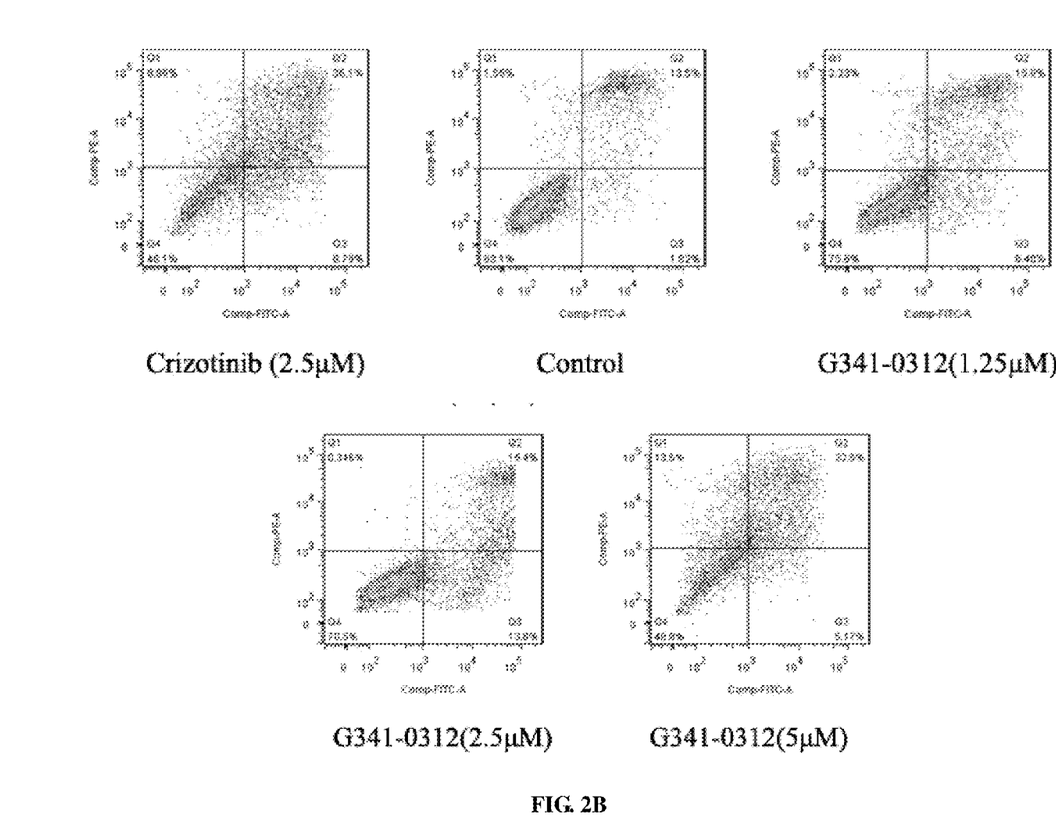
Figure 3:
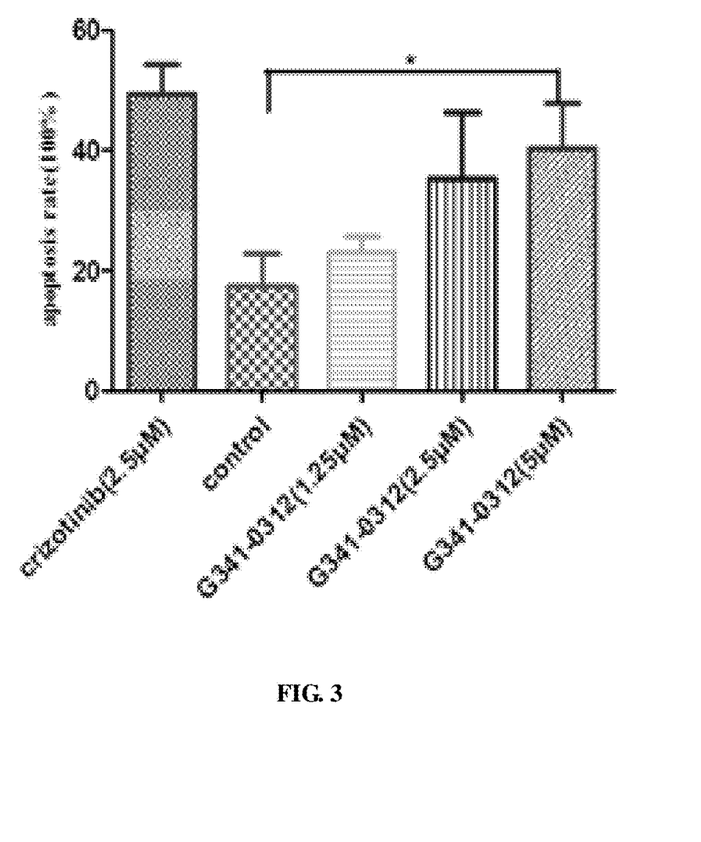
FIG. 3 shows rate of apoptosis of HCC78 cells having treated with compound of Formula I of the present invention.

The compound of Formula I of the present invention, as a potent ROS1 inhibitor, induces apoptosis in cancerous cells. Apoptosis assay is performed on HCC78 cells to demonstrate the potent ROS1 inhibitory effect of the present invention. HCC78 cells ($1.0 \times 10^5$ cells/well) are allowed to attach to a 6-well plate for 24 h, and the cells are treated with the various concentrations of the present compound for an additional 72 h. At the end of incubation, the cells are harvested by trypsinization and washed twice with ice-cold PBS. After centrifugation and removal of the supernatants, cell pellets are resuspended in 100 μL 1× Annexin-binding buffer. 2 μl Annexin-V FITC and 2 μl PI (100 μg/ml) are added and incubated in the dark at room temperature for 15 min, before further addition of 400 μl of 1× Annexin-binding buffer. The stained cells are analyzed quantitatively using a flow cytometer (BD Biosciences, San Jose, Calif., USA). FIG. 2A shows fluorescence images of HCC78 cells having treated with the present compound of Formula I (G341-0312) at 1.25 μM, 2.5 μM and 5 μM; 2.5 μM Crizotinib (a known ROS1 inhibitor as positive control) and DMSO (control, negative control). The results show that HCC78 cells having treated with the present compounds detach from the surface and are small at 2.5 μM of G341-0312. Such cell morphology indicates apoptosis. For a more quantitative view, flow cytometry analysis is performed. As seen in FIG. 2B and FIG. 3, the present compound of Formula I exhibits anti-cancer ability through induction of apoptosis on HCC78 cells in a concentration dependent manner. A significant apoptosis level is observed in HCC78 cells having treated with the compound of the present invention.

The compound of Formula I of the present invention also suppresses ROS1 phosphorylation and anti-apoptotic and growth signaling pathways that are downstream to ROS1. Previous studies demonstrate that ROS1 fusion kinases signal is activated through the tyrosine phosphatase Src homology-2 domain containing protein tyrosine phosphatase-2 (SHP2) and causes activation of the downstream MEK/ERK, PI3K/AKT/mTOR, and JAK/STAT3 signaling axes. Together, these downstream signaling pathways promote tumor cell survival and proliferation. Therefore, inhibition of these downstream signaling pathways suppresses growth and proliferation of cancer cells and results in anti-cancer effect. The effect of the compound of Formula I on ROS1 phosphorylation as well as signaling biomolecules downstream of ROS1 are studied.

The cells are planted on 6-well plate, allowed to attach for 24 hours, and treated with the various concentrations of compound of Formula I for 72 hrs. Cells are washed twice with cold PBS then lysed in RIPA lysis buffer containing protease and phosphatase inhibitors. Protein concentration of the cell lysates are measured using the Bio-Rad protein Assay kit (Bio-Rad, Philadelphia, Pa., USA). After equalizing the protein concentrations of the samples, 5× laemmli buffer is added and boiled at 100° C. for 5 min. Equal amounts of protein samples (30 μg) are subjected to SDS-PAGE of a 10% gel. The separated proteins are transferred to a nitrocellulose (NC) membrane, which is then exposed to 5% non-fat dried milk in TBS containing 0.1% Tween 20 (0.1% TBST) for 1 h at room temperature, followed by overnight incubation at 4° C. with primary anti-bodies to GAPDH, phospho-AKT, AKT, photspho-ROS1, ROS1, phospho-ERK, ERK, photspho-STAT3, STAT3. After washing 3 times by TBST (5 mins/time), the membranes are incubated for 1 hour at room temperature with the secondary fluorescent antibodies (1:10000 dilutions) to rabbit or mouse. The signal intensity of the membranes is detected by an LI-COR Odessy scanner (Belfast, Me., USA).

Figure 4:
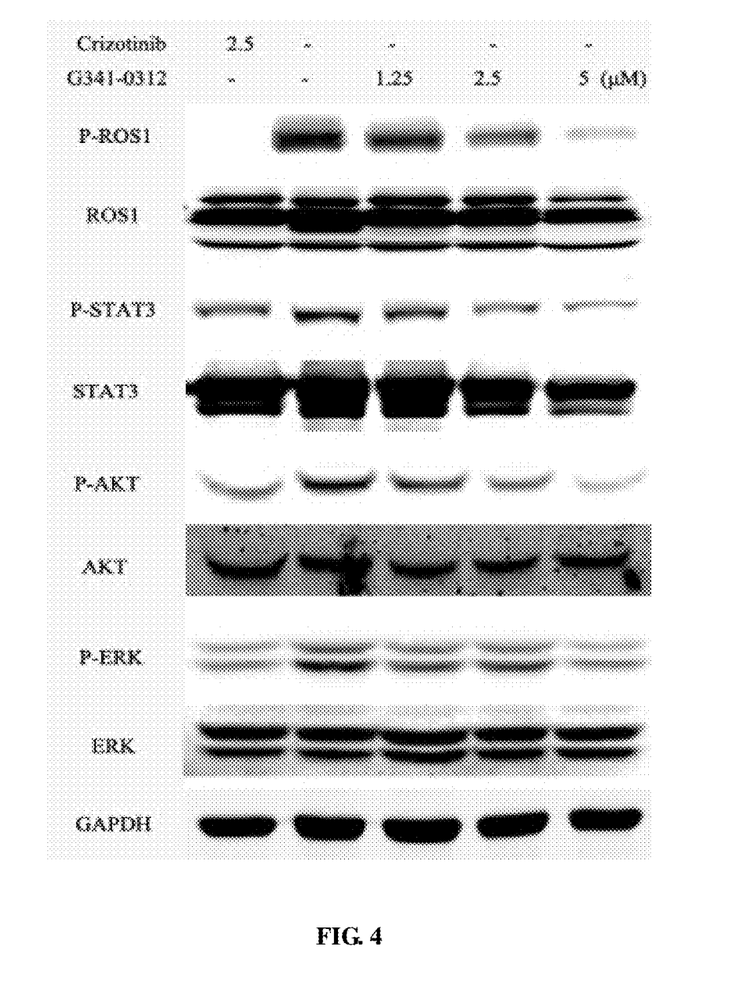
FIG. 4 is a western blot showing the binding affinity of the compound of Formula I of the present invention to ROS1 and other signaling molecules downstream to ROS1.

Treatment of HCC78 cells with compound of Formula I (G341-0312) leads to a dose-dependent decrease of ROS1 phosphorylation as well as its downstream signaling molecules Erk1/2, STAT3 and AKT signaling, further supporting the anti-cancer effect of G341-0312 (FIG. 4). Crizotinib is used as positive control.

The binding mechanism of the present compound of Formula I to ROS1 is studied. Molecular docking calculation is performed to study the interaction between compound of Formula I and ROS1 by Induced Fit Docking module in Schrodinger software (Schrodinger, Inc., New York, N.Y., 2009). Compound of Formula I is prepared and optimized in the LigPrep module. During the induced fit docking, centroid of the crizotinib is defined as the active site and the pose of ligand is valued with XP docking score. The pose with the highest score is selected for further analysis. The 3D structure of ROS1 is derived from the PDB database (PDB ID: 3ZBF) and prepared using the Protein Preparation Wizard.

Figure 5A:
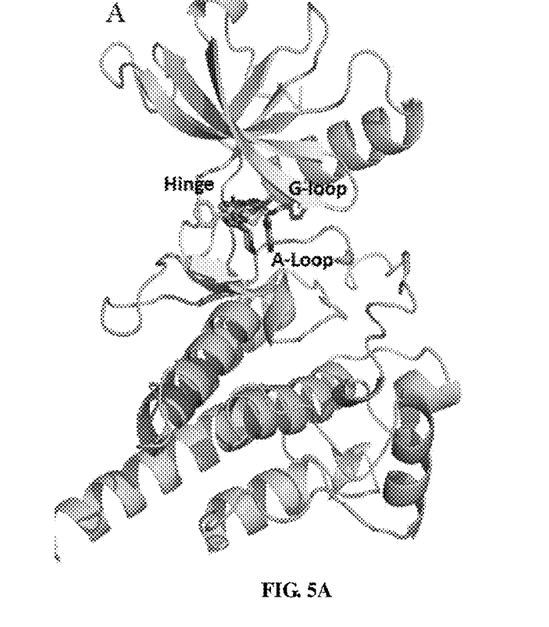
Figure 5B:
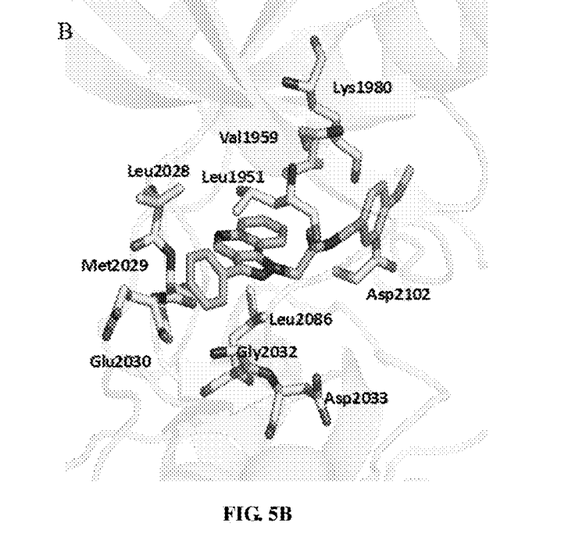

The present compound of Formula I has a similar binding mechanism to ROS1 as Crizotinib. The docking scores of the present compound and Crizotinib to ROS1 are −11.157 and −9.674 Kcal/mol, respectively. The present compound is shown to have a better binding affinity to ROS1 than Crizotinib. As seen in FIG. 5A, the pyridine groups of the both compounds have hydrogen bond to Met2029 in the hinge region. The phenyl group and the anisole group of compound of Formula I forms extra hydrophobic interaction with the hinge and G-loop, respectively. As shown in FIG. 5B, residues Leu 2028, Met2029, Glu2030, Gly2032, Asp2033 in the hinge region have contact with the compound of Formula I, while the residues Leu1951, Leu1959 in the G-loop form hydrophobic interaction with the present compound. Other residues, such as Lys1980, Asp2102, Leu2086, also make a great contribution to the binding of the present compound.

In the above examples, differences are analyzed by on-way ANVOA. All statistical analyses are carried out using Graph Prim5.0. P<0.05 was considered significant.

INDUSTRIAL APPLICABILITY

The present invention provides a new inhibitor, compound of Formula I, that can specific target oncogenic ROS1 kinase, which exhibits potent anti-cancer activity, and notably in NSCLC cell with ROS1 fusion gene. The compound of Formula I of the present invention significantly suppresses ROS1 phosphorylation as well as its downstream anti-apoptotic and growth signaling biomolecules, including PI3K/AKT, MEK/ERK and JAK/STAT3 signaling pathways. The present compound shows relatively low toxicity to normal lung epithelial cells, which can be used as anti-cancer drug for targeting subgroup of cancer patients who harbor different forms of ROS1 chromosomal rearrangement.

The invention claimed is:

1. A method of treating a ROS1 positive non-small cell lung cancer comprising administering a composition comprising a compound of Formula I:

to a ROS1 positive non-small cell lung cancer patient.

2. A method of inducing apoptosis in non-small cell lung cancer cells comprising contacting a composition comprising a compound of Formula I:

to said non-small cell lung cancer cells.

3. The method of claim 2, wherein said non-small cell lung cancer cells have an oncogenic ROS1 gene resulted from chromosome rearrangement and/or gene fusion.

* * * * *